(12) United States Patent
Sauer et al.

(10) Patent No.: US 7,677,078 B2
(45) Date of Patent: Mar. 16, 2010

(54) LINE-BASED CALIBRATION OF ULTRASOUND TRANSDUCER INTEGRATED WITH A POSE SENSOR

(75) Inventors: Frank Sauer, Princeton, NJ (US); Ali Khamene, Princeton, NJ (US); Oliver Kutter, München (DE); Sebastian Kassner, Nackenheim (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 394 days.

(21) Appl. No.: 11/649,391

(22) Filed: Jan. 3, 2007

(65) Prior Publication Data

US 2008/0287787 A1    Nov. 20, 2008

Related U.S. Application Data

(60) Provisional application No. 60/764,572, filed on Feb. 2, 2006.

(51) Int. Cl.
*G01M 1/14* (2006.01)
(52) U.S. Cl. .................... 73/1.86; 73/1.83; 73/1.82
(58) Field of Classification Search ............ 73/1.86, 73/1.83, 1.82
See application file for complete search history.

(56) References Cited

U.S. PATENT DOCUMENTS

| | | | | | |
|---|---|---|---|---|---|
| 4,660,419 A | * | 4/1987 | Derkacs et al. | ............... | 73/622 |
| 2004/0254458 A1 | * | 12/2004 | Govari | ............... | 600/437 |

* cited by examiner

*Primary Examiner*—Robert R. Raevis
*Assistant Examiner*—Nathaniel Kolb
(74) *Attorney, Agent, or Firm*—Donald B. Paschburg

(57) ABSTRACT

Apparatus for calibrating an ultrasound transducer providing B-scans for two-dimensional (2D) images, includes: an ultrasound probe for providing B-scans; a position sensing device, the position sensing device being attached to the ultrasound probe and operating as part of a position sensing system in cooperation with a fixed sensing control unit, for labeling the B-scans with their respective relative positions and orientations (pose); a phantom marker for being imaged by the ultrasound probe for providing measurements which together with known physical properties of the phantom marker are used to derive calibration information for relating measurement data from the position sensing device to the poses of the B-scans to construct a 3D image; and the phantom marker comprising an encoded line object with distinctive calibration characteristics indicative of position along the line object, wherein the line object is disposed in a generally circumferential manner about a common axis with the probe.

33 Claims, 6 Drawing Sheets

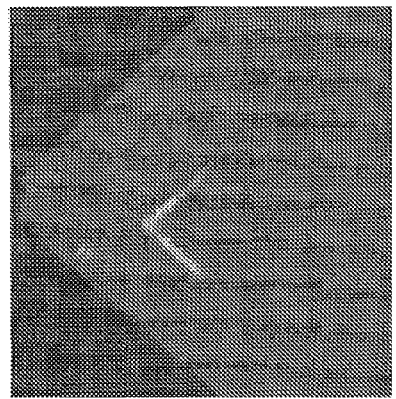 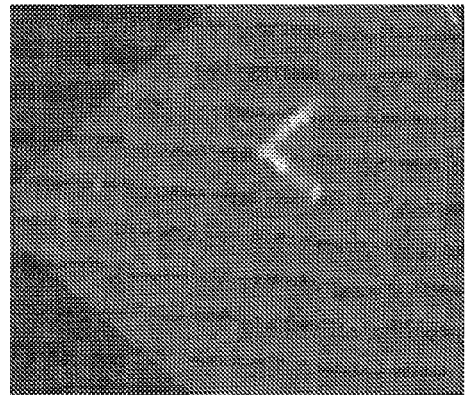
FIG. 5(a)        FIG. 5(b)

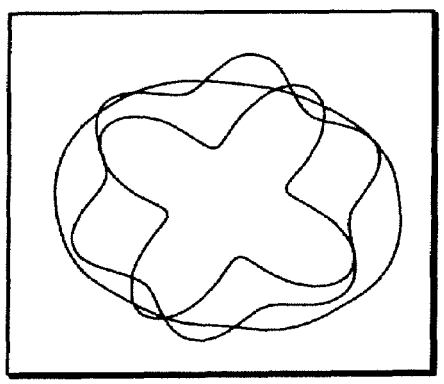
(a)
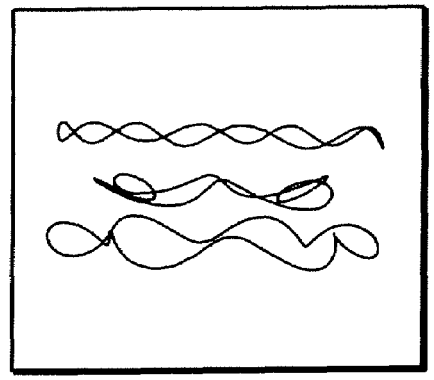
(b)
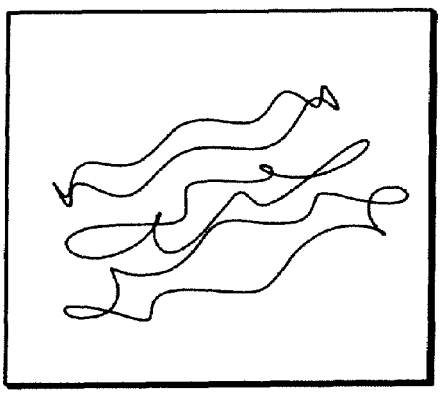
(c)
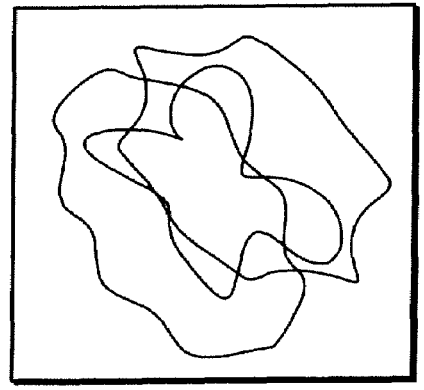
(d)
FIG. 6

LINE-BASED CALIBRATION OF ULTRASOUND TRANSDUCER INTEGRATED WITH A POSE SENSOR

CROSS-REFERENCE TO RELATED APPLICATION AND CLAIM OF PRIORITY

Specific reference is hereby made to copending U.S. Provisional Patent Application No. 60/764,572, filed Feb. 2, 2006, in the names of inventors FRANK SAUER, ALI KHAMENE, OLIVER KUTTER and SEBASTIAN KASSNER, and entitled Line-based Calibration of Ultrasound Transducer Integrated with Pose Sensor, and whereof the disclosure is hereby incorporated herein by reference and whereof the benefit of priority is claimed.

FIELD OF THE INVENTION

The invention relates generally to three-dimensional (3D) ultrasound imaging, and more particularly, to 3D imaging acquired with an ultrasound transducer whose pose is being monitored by a tracking system.

BACKGROUND OF THE INVENTION

Intracardiac ultrasound is routinely used to monitor ablation procedures in the heart chambers. For example, a commercial intracardiac ultrasound system is the AcuNav™ of Siemens Medical Solutions.

The AcuNav™ transducer acquires two-dimensional (2D) B-mode images, and the corresponding ultrasound system displays these 2D images in real-time. Nevertheless, with only a 2D slice of the heart chamber visible at a time, the usefulness and usability of the system is in some ways limited. It is desirable to have a 3D image available. Image understanding (i.e. localizing anatomical features in the images), placement of the transducer, and observation of other catheters are easier to do with a 3D image.

A B-mode transducer as herein referred to is a brightness transducer for producing a typical grey-scale image. A preferred way of acquiring 3D ultrasound images, in the absence of transducers that can directly scan volumes, is to move a B-mode transducer around while tracking its pose (position and orientation), and compound the 2D images into a 3D image according to the pose information. For this "freehand 3D ultrasound", as it is commonly called in the literature, calibration has to be performed. Calibration determines the relative pose of a magnetic pose sensor and an ultrasound image. Various methods have been described to perform the calibration. Calibration is, for example, described in Prager, R. W., R. N. Rohling, et al. (1998). "Rapid calibration for 3-D freehand ultrasound." Ultrasound in Medicine and Biology 24 (6): 855-869.

Methods described in the literature have, however, typically only been developed and tested for prototype work, and are only suitable for calibrating a small quantity of prototype assemblies.

BRIEF SUMMARY OF THE INVENTION

As will hereinafter be explained in further detail, the present invention relates to a line-based calibration of an ultrasound transducer integrated with pose sensor, disclosed in the aforesaid copending U.S. Provisional Patent Application No. 60/764,572.

It is herein recognized that, preferably, the calibration process is performed as part of the manufacturing process.

It is also herein recognized that, for practical mass production, there is a need for a calibration process that can be performed as part of the fabrication of catheters, and that known methods in accordance with basic principles are not very practical for a mass production and mass calibration scenario. Typically each catheter equipped with an ultrasound transducer and a magnetic pose sensor has to be calibrated individually, and hence there is the need for an efficient calibration process.

As will also be hereinafter explained, the present invention also relates to calibration aspects disclosed in U.S. provisional patent application No. 60/657,753 filed Mar. 1, 2005 in the name of Frank Sauer, Ali Khamene, et al., and entitled "System for Visualization of 3D intracardiac ultrasound": and to further aspects of calibration, including further apparatus and methods for practical sensors and the practical industrial calibration of catheters with integrated ultrasound transducers and pose disclosed in U.S. provisional patent application No. 60/718,808 filed Sep. 20, 2005 in the name of Frank Sauer, Ali Khamene, et al. and entitled "Calibration of ultrasound transducer integrated with pose sensor,", whereof the disclosures of the two foregoing provisional patent applications are hereby incorporated herein by reference.

In accordance with an aspect of the present invention, the invention comprises an ultrasound imaging type of system including a catheter based B-mode ultrasound transducer, equipped with a miniature sensor for magnetic tracking, and a processing system and control system to drive the transducer, and process the acquired data to generate images.

In accordance with another aspect of the present invention, a system for 3D ultrasound imaging comprises an electromagnetic tracking system comprising an electromagnetic field generator, miniature sensors, and a processing unit to determine the 6 degree-of-freedom pose (position and orientation) of the sensors.

In accordance with another aspect of the present invention, a processing system for calculation of the calibration parameters, which receives pose information and (time synchronized) ultrasound images, and includes an image processing unit (or software program) to extract the position of markers in the ultrasound images In order to compound a 3D image correctly, the correct pose (position and orientation) of the 2D images from the tracking information should be derived. The tracking information initially provides only the pose of the magnetic pose sensor in a world coordinate system. A calibration process is needed to determine the pose of the 2D ultrasound image in the coordinate system of the magnetic pose sensor, and also one or two scale factors for the correct geometric size of the image pixels. With this calibration information, the 2D ultrasound image can be mapped into the 3D world coordinate system according to the tracking information.

Calibration for freehand 3D ultrasound has been extensively described in the literature. See, for example, the aforementioned publication by Prager et al. In accordance with another aspect of the present invention, a calibration phantom includes well defined geometric structures and is set up so that these structures are known in the world coordinate system of the tracker. It is imaged with a tracked ultrasound transducer, and the structures seen in the images are brought into correspondence with the actual structures of the phantom.

In accordance with another aspect of the present invention, as the locations of these structures and the position of the magnetic pose sensor attached to the transducer are known in the world coordinate system of the magnetic tracking system, one can solve for the pose and scale of the 2D ultrasound image in the coordinate system of the magnetic pose sensor.

In accordance with another aspect of the invention, apparatus for calibrating an ultrasound transducer providing B-scans for two-dimensional (2D) images, the apparatus comprises: an ultrasound probe for providing B-scans; a position sensing device, the position sensing device being attached to the ultrasound probe and operating as part of a position sensing system in cooperation with a fixed sensing control unit, for labeling the B-scans with their respective relative positions and orientations (pose); a phantom marker for being imaged by the ultrasound probe for providing measurements which together with known physical properties of the phantom marker are used to derive calibration information for relating measurement data from the position sensing device to the poses of the B-scans to construct a 3D image; and the phantom marker comprising an encoded line object with distinctive calibration characteristics indicative of position along the line object, wherein the line object is disposed in a generally circumferential manner about a common axis with the probe.

In accordance with another aspect of the invention, the probe and the phantom marker are mounted for enabling mutual rotation with respect to one another about the common axis.

In accordance with another aspect of the invention, the encoded line object comprises a plurality of generally circular modulated loops disposed circumferentially about the common axis and exhibiting respective varying amounts of modulation along their respective lengths.

In accordance with another aspect of the invention, the modulated loops exhibit respective degrees of radial swinging relative to an unmodulated radial line.

In accordance with another aspect of the invention, the modulated loops exhibit respective degrees of swinging up and down relative to an unmodulated circular line.

In accordance with another aspect of the invention, the modulated loops exhibit a triangular cross-section whereof a point is oriented towards the probe for providing an ultrasound image of the point and the triangular cross-section.

In accordance with another aspect of the invention, apparatus is included for processing the ultrasound image of the point and the triangular cross-section for enabling automatic localization of the ultrasound image of the point.

In accordance with another aspect of the invention, apparatus is included for performing the automatic localization of the ultrasound image of the point.

In accordance with another aspect of the invention, apparatus for introducing an offset between the axis of the line object and the axis of the transducer is included.

In accordance with another aspect of the invention, apparatus for modulating the offset between the axis of the line object and the axis of the transducer is included.

In accordance with another aspect of the invention, apparatus for calibrating an ultrasound transducer providing B-scans for two-dimensional (2D) images, the apparatus comprising: a sensing device attached to the transducer, the sensing device cooperating with a fixed sensing unit for providing an output for labeling respective B-scans with their respective relative positions and orientations (poses); a calibration phantom bath including a phantom therein, the transducer being immersed in the bath for imaging the phantom; the phantom comprising a line object with distinctive encoding indicative of position along the line object, the line object being generally disposed about an axis substantially concentric with an axis of rotation of the transducer and in the field of view of the transducer; apparatus for enabling rotation of one of the transducer and the phantom about the axis of rotation for obtaining successive B-scan images of the line object exhibiting the calibration characteristics; apparatus for rotating one of the transducer and the phantom about the axis of rotation for obtaining successive B-scan images of the line object exhibiting the calibration characteristics; apparatus for deriving relative transducer pose information from the calibration characteristics in the successive B-scan images; and apparatus for deriving transducer pose information relative to the fixed sensing unit by combining the output thereof and the relative transducer pose information.

In accordance with another aspect of the invention, the line object forms a loop in a generally circumferential form about the axis; and the line object exhibits a cross-section sufficient for providing an adequate ultrasound image in the B-scan images.

In accordance with another aspect of the invention, the line object exhibits a cross-section having a V-shape exhibiting a point and the point is oriented towards the transducer.

In accordance with another aspect of the invention, apparatus is included for processing the ultrasound image of the point and the triangular cross-section for enabling automatic localization of the ultrasound image of the point. Apparatus is included for performing the automatic localization of the ultrasound image of the point.

In accordance with another aspect of the invention, the encoding comprises the line object being formed into a modulated circular form exhibiting a varying amount of modulation along its length. In accordance with another aspect of the invention, the line object comprises a plurality of closed loops in a generally circumferential form about the axis. In accordance with another aspect of the invention, the line object comprises a plurality of loops with a cross-section sufficient for providing an adequate ultrasound image in the B-scan images.

In accordance with another aspect of the invention, the loops have a cross-section having a V-shape exhibiting a point oriented towards the transducer. The loops comprise a corresponding plurality of modulated circular forms exhibiting respective varying amounts of modulation along their respective lengths as a function of angular position around the axis. The loops comprise a corresponding plurality of modulated circular forms exhibiting respective varying amounts of modulation along their respective lengths.

In accordance with another aspect of the invention, the modulated circular forms exhibit respective degrees of radial swinging relative to an unmodulated radial line.

In accordance with another aspect of the invention, the modulated circular forms exhibit respective degrees of swinging up and down relative to an unmodulated circular line.

In accordance with another aspect of the invention, the modulated circular forms exhibit respective degrees of swinging up and down relative to an unmodulated circular line, wherein a given modulated circular form is described as follows:

if the z-axis represents a common axis for circles in a Cartesian coordinate system, a periodically modulated circle can be described by the following parametric equations:

$$x(\phi)=\cos(\phi)(r+a\cdot\sin(n\cdot\phi+p))$$

$$y(\phi)=\sin(\phi)(r+a\cdot\sin(n\cdot\phi+p))$$

$$z(\phi)=a_z\cdot\sin(n_z\cdot\phi+p_z)+c_z$$

where $\phi \in \{-\pi,\pi\}$, n and $n_z \in N$, and r is the circle radius and the modulation amplitudes for radius r and height z are a and $a_z$, and the parameters n and $n_z$ describe how many full periods of modulation occur on the circle, and p and $p_z$ allow for phase shifts of the modulation.

In accordance with another aspect of the invention, the modulated circular forms exhibit a configuration of the respective varying amounts of modulation that does not exhibit periodicity within a complete rotation around the axis.

In accordance with another aspect of the invention, apparatus for calibrating an ultrasound transducer providing B-scans for two-dimensional (2D) images, comprises: ultrasound probe apparatus for providing B-scans; apparatus for sensing a position and being attached to the ultrasound probe apparatus and operating as part of a position sensing system in cooperation with a fixed sensing control apparatus, for labeling the B-scans with their respective relative positions and orientations (pose); phantom marker apparatus for being imaged by the ultrasound probe apparatus for providing measurements which together with known physical properties of the phantom marker apparatus are used to derive calibration information for relating measurement data from the apparatus for sensing a position to the poses of the B-scans to construct a 3D image, and the phantom marker apparatus comprises an encoded line apparatus with distinctive calibration characteristics indicative of position along the encoded line apparatus, wherein the encoded line apparatus is disposed in a generally circumferential manner about a common axis with the ultrasound probe apparatus.

In accordance with another aspect of the invention, a method for line-based calibration of an ultrasound transducer for two-dimensional (2D) images, the method comprises: immersing a transducer in a calibration phantom bath; encoding a calibration parameter at respective portions of a line object such that the parameter is indicative of a respective associated portion of the line object; wrapping the line object circumferentially about a substantially concentric axis with the transducer in the bath such that the line object is visible in successive 2D images as the transducer is rotated about the axis; deriving values of the calibration parameter from respective 2D images; and calculating the pose of a 2D image from a respective value of the calibration parameter.

In accordance with another aspect of the invention, a method for deriving the pose of a two-dimensional (2D) ultrasound image from a transducer, the method comprises: setting up a known tracking system having a known coordinate correspondence with a calibration phantom bath; calculating the pose of the calibration phantom bath; immersing a transducer in the calibration phantom bath; encoding a calibration parameter at respective portions of a line object such that the parameter is indicative of a respective associated portion of the object; wrapping the line object about a substantially concentric axis with the transducer in the bath such that the line object is visible in successive 2D images as the transducer is rotated about the axis; deriving values of the calibration parameter from respective 2D images; calculating a pose of a given 2D image relative to the calibration phantom bath from a respective value of the calibration parameter derived from the given 2D image; and calculating a pose of the given 2D image relative to the tracking system by utilizing the pose of a given 2D image relative to the calibration phantom bath.

In accordance with another aspect of the invention, a method for deriving the pose of a two-dimensional (2D) ultrasound B-mode image from a transducer, comprises: inserting a catheter with an associated magnetic pose sensor into a calibration phantom bath; rotating the catheter about its axis to get a planar marker configuration into the field-of-view; acquiring an image of markers by utilizing the transducer, and a corresponding pose; acquiring information from a magnetic pose sensor with a magnetic tracking system; locating 2D marker positions in the B-mode image; calculating 3D marker positions in a coordinate system of the magnetic pose sensor; and calculating pose and scale of the B-mode image in the coordinate system of the magnetic pose sensor from 2D-3D correspondences.

In accordance with another aspect of the invention, a method for calibrating an ultrasound transducer providing B-scans for two-dimensional (2D) images, comprises: attaching to the transducer a sensing device cooperating with a fixed sensing unit for providing an output for labeling respective B-scans with their respective relative positions and orientations (poses); immersing the transducer in a calibration phantom bath for imaging a phantom; encoding a line object with distinctive calibration characteristics indicative of position along the line object; wrapping the line object about an axis substantially concentric with an axis of rotation of the transducer and in the field of view of the transducer; rotating the transducer about the axis of rotation for obtaining successive B-scan images of the line object exhibiting the calibration characteristics; deriving relative transducer pose information from the calibration characteristics in the successive B-scan images; and deriving transducer pose information relative to the fixed sensing unit by combining the output thereof and the relative transducer pose information.

In accordance with another aspect of the invention, a phantom marker for being imaged by an ultrasound probe having an axis and providing B-scans, the phantom marker providing measurements which together with known physical properties of the phantom marker are used to derive calibration information for relating measurement data from a position sensing device to poses of the B-scans to construct a 3D image, wherein the phantom marker comprises an encoded line object with distinctive calibration characteristics indicative of position along the line object, wherein the line object is disposed in a generally circumferential manner about the axis.

In accordance with another aspect of the invention, apparatus for calibrating an ultrasound transducer providing B-scans for two-dimensional (2D) images, comprises: an ultrasound probe for providing B-scans; a position sensing device, the position sensing device being attached to the ultrasound probe and operating as part of a position sensing system in cooperation with a fixed sensing control unit, for labeling the B-scans with their respective relative positions and orientations (pose); a phantom marker for being imaged by the ultrasound probe for providing measurements which together with known physical properties of the phantom marker are used to derive calibration information for relating measurement data from the position sensing device to the poses of the B-scans to construct a 3D image, and the phantom marker comprising markers of a planar marker distribution having a known position in a magnetic coordinate system such that the markers do not occlude each other in the field-of-view of the ultrasound transducer.

In accordance with another aspect of the invention, apparatus for calibrating an ultrasound transducer providing B-scans for two-dimensional (2D) images, comprises: an ultrasound probe for providing B-scans; a position sensing device, the position sensing device being attached to the ultrasound probe and operating as part of a position sensing system in cooperation with a fixed sensing control unit, for labeling the B-scans with their respective relative positions and orientations (pose); a phantom marker for being imaged by the ultrasound probe for providing measurements which together with known physical properties of the phantom marker are used to derive calibration information for relating measurement data from the position sensing device to the poses of the B-scans to construct a 3D image, and the phantom marker comprises line markers arranged in a line marker plane such that an ultrasound imaging plane intersects the line marker plane with the ultrasound plane essentially perpendicular to the line marker plane, the markers comprising a set of strings running at different angles in a string marker plane, closer to horizontal than vertical and are imaged as small dots where they intersect an ultrasound plane, and wherein the ratio of distances between respective ones of the dots is uniquely related to the location where the ultrasound plane intersects the string plane, and hence, gives unique information on the angle under which the ultrasound transducer is imaging the string plane from its location.

BRIEF DESCRIPTION OF THE SEVERAL VIEWS OF THE DRAWINGS

The invention will be more fully understood from the detailed description following, in conjunction with the Drawing, in which

FIG. 5 shows ultrasound images with V-shaped marker cross-sections; and

FIG. 6 shows modulated circles in 3D in different views.

DETAILED DESCRIPTION OF THE INVENTION

Briefly reviewing the above description, when a 3D free-hand ultrasound is used, a position sensing device, which operates as part of a position sensing system, is attached to a conventional ultrasound probe which is utilized for providing B-scans. The position sensing device, for example the receiver of an electromagnetic pose sensor which cooperates with a fixed transmitter, enables the B-scans to be labeled with their respective relative positions and orientations (pose). This makes it possible to insert the B-scans into a 3D voxel array which may then be viewed or visualized in conventional ways, including plane-slicing, volume rendering, or surface rendering. An important requirement in free-hand imaging systems is calibration, that is, determining the pose of the B-scan with respect to the position sensing system.

Calibration is typically performed by imaging a phantom which is an artificial object having defined, known physical properties and/or dimensions. Measurements resulting from imaging and examination of the phantom, together with its known physical properties serve to derive calibration information for relating the sensor measurements to the positions of the B-scans in constructing a 3D image.

The introductory part of the present detailed description of the invention starts with a review of the disclosure of the two aforementioned provisional patent applications, Nos. 60/657,753 and 60/718,808, whereof FIGS. 1-4 are essentially the same as the corresponding FIGS. 1-4 of the present application, so that reference to any of FIGS. 1-4, simply made, refers to the like number figure in the two aforementioned provisional patent applications Nos. 60/657,753 and 60/718,808 and in the aforementioned copending provisional patent application No. 60/764,572, as well as in the present application.

Figure 1:
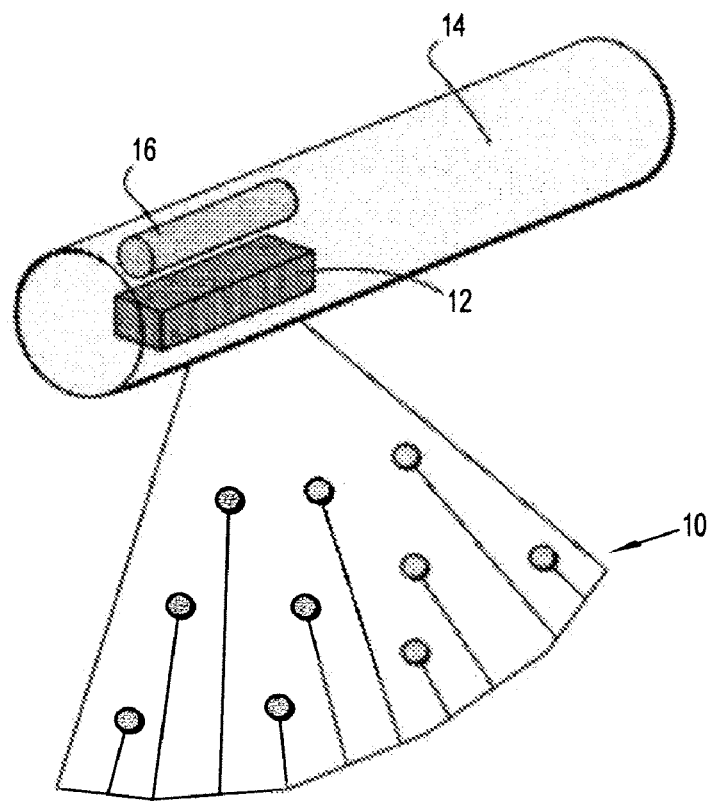
FIG. 1 shows a planar marker distribution in the field-of-view of an ultrasound transducer.

A calibration phantom contains a set of markers, which can be easily localized and identified in the ultrasound image. The markers should also be well distributed in the image. In a preferred embodiment of the calibration phantom, the arrangement of the markers is planar. FIG. 1 shows a planar marker distribution 10 in the field-of-view of an ultrasound transducer 12 embedded in the tip of a catheter 14, together with an electro-magnetic sensor 16. The markers of planar marker distribution 10 have a known position in a magnetic coordinate system. This is a possible planar arrangement of calibration markers which are well distributed and do not occlude each other in the field-of-view of the ultrasound transducer.

Figure 2:
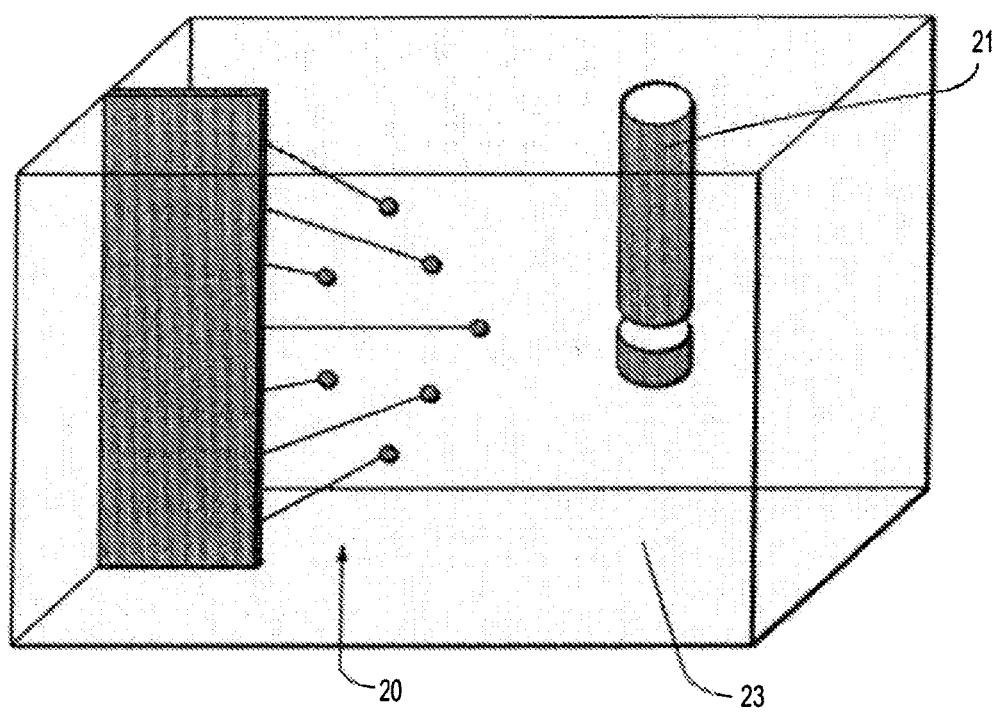
FIG. 2 shows a marker arrangement as a part of a waterbath calibration phantom.

FIG. 2 shows a basic arrangement of a calibration phantom, with a marker arrangement 20 as part of a water-bath calibration phantom, with catheter access from above through a cylindrical guide 21.

The phantom comprises a tank filled with an ultrasound transmissive liquid 23. Submerged in the tank is the marker distribution. Access for the catheter is provided via cylindrical guide 21, preferably through a lid (not shown) on top of the phantom. The inner diameter of guide 21 is slightly larger than the outer diameter of the catheter, as a sliding fit, for example, so that the guide holds the axis of the inserted catheter in a well defined position. There is a mechanical stop (not shown) for the tip of the catheter, so that the catheter will be inserted to a pre-defined depth. Planar marker arrangement 20 is aligned with cylindrical guide 21, that is, the axis of the guide lies in the plane of the planar marker configuration. The guide contains a window, that is, there is a gap between the guide and the mechanical stop, so as to allow the ultrasound transducer an unobstructed view of the marker configuration. After insertion, the catheter is turned about its axis into the orientation wherein the 2D ultrasound view shows an optimal image of the planar marker configuration. With the precise angular alignment around the axis, one of the pose parameters is determined; the others, and the scale parameters, can be calculated based on the 2D-3D point correspondences of 2D marker locations in the planar image and 3D marker locations inside the phantom, taking the magnetic tracking information into account.

In effect, the calibration process may also be considered in the following manner:

what is known is the geometry of a phantom, pose (position and orientation) of the phantom in a magnetic coordinate system; and what are not known are the pose and scale of a B-mode image in a coordinate system of a magnetic pose sensor.

The process then comprises:

inserting a catheter into a phantom;

rotating the catheter about its axis to get planar a marker configuration into the field-of-view;

acquiring an image of markers (with an ultrasound transducer) and corresponding pose;

acquiring information from a magnetic pose sensor (with a magnetic tracking system): for best results, one can average over a set of images acquired in the same position;

locating 2D marker positions in a B-mode image;

calculating 3D marker positions in a coordinate system of the magnetic sensor; and calculating pose and scale of the B-mode image in the coordinate system of the magnetic sensor from 2D-3D correspondences.

The calibration with this calibration phantom is fast and efficient. It can be automated, for example, with a computer controlled system that includes a mechanical arm that grasps the catheter and turns it into the correct position towards the marker configuration (based on image processing of the 2D ultrasound images). The system captures the final calibration image that shows the optimal view of the marker configuration, calculates and stores the catheters calibration parameters, and pulls the catheter back out of the calibration phantom. The process is repeated with each individual catheter.

The user of the catheter needs to have both the catheter and the calibration information. A preferred and automated way of providing the calibration information is to store it in an EPROM that is part of the catheter assembly. During use, the catheter assembly has electrical connections to the overall control and visualization system, for transmission of magnetic tracking and ultrasound imaging signals. Extra electrical connections can be provided for transmission of EPROM information. In a preferred embodiment, the catheter assembly contains a single electric plug that can be plugged into a corresponding jack of the control and visualization system and establishes all the electrical connections. Data transmission may alternatively, or in addition, be multiplexed, for example by time or frequency division multiplexing, for transmission by way of a single data port.

The catheter needs to be sterilized for use on humans. It is possible to conduct the calibration process in a sterile environment if there are reasons to perform calibration after sterilization. For this, the sterilizable calibration phantom is made sterile and contains a sterile liquid.

An alternative embodiment of the calibration phantom employs a marker configuration that is not planar, but extends into the third dimension. The markers are arranged in a way that the catheter does not have to be precisely aligned around its axis to get an optimal view of the markers. Instead, the markers are distributed in a way such that they code the angle information.

Figure 3:
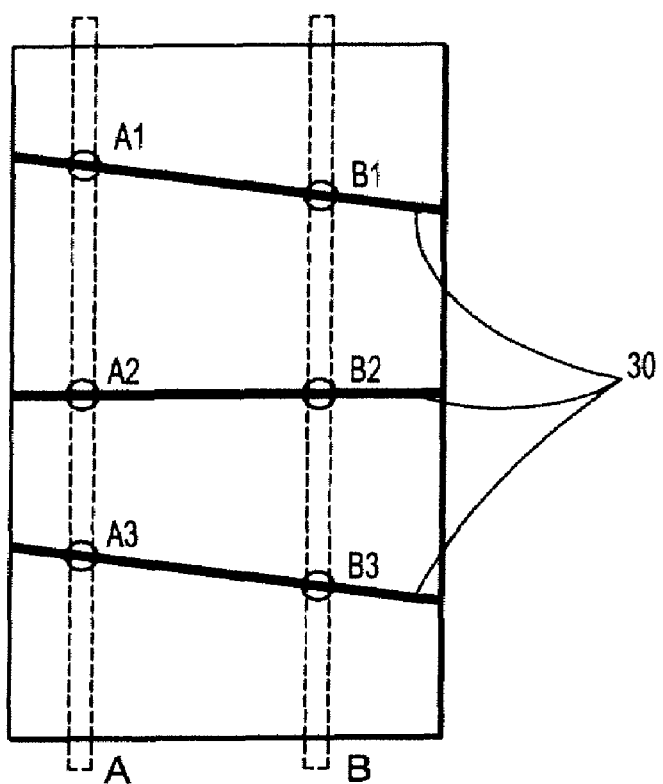
FIG. 3 illustrates the principle of coding position/angle information in the marker configuration.

FIG. 3 illustrates the principle of coding position/angle information in the marker configuration. The line markers (bold lines 30) are arranged in a line marker plane. The ultrasound imaging plane intersects the line marker plane, for example in positions A or B (dashed lines), with the ultrasound plane essentially perpendicular to the line marker plane. Intersections between line markers and ultrasound plane in positions A and B are circled and marked A1, A2, A3 and respectively B1, B2, B3.

In one embodiment, the markers comprise a set of thin strings, arranged in a plane whose normal vector is perpendicular to the catheter and perpendicular to the normal vector of the planar marker configuration described earlier. The strings run at different angles in this string marker plane, closer to horizontal than vertical and are imaged as small dots where they intersect the ultrasound plane. As the strings are in one plane, the dots appear along one line. The ratio of the distances between the dots is uniquely related to the location where the ultrasound plane intersects the string plane, and hence, gives unique information on the angle under which the ultrasound catheter is imaging the string plane from its location inside the cylindrical guide. In a preferred embodiment, several of these string planes are arranged in parallel to cover the depth of field of the ultrasound image. The width of the string planes is chosen to cover about 10-30 degrees of axial rotation of the ultrasound catheter. A single 2D ultrasound image yields the complete information for calibration. Preferably, however, several images are taken at different angles (with the string planes within the field of view) to optimize the results of the calibration procedure.

Figure 4A:
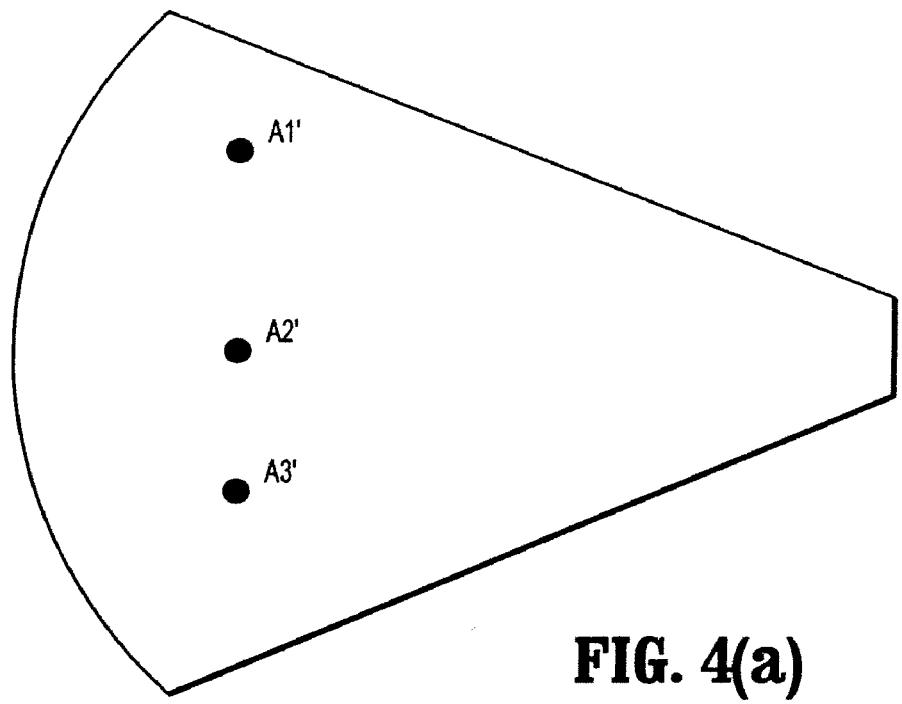
FIG. 4 shows in schematic form ultrasound images corresponding to positions in FIG. 3.
Figure 4B:
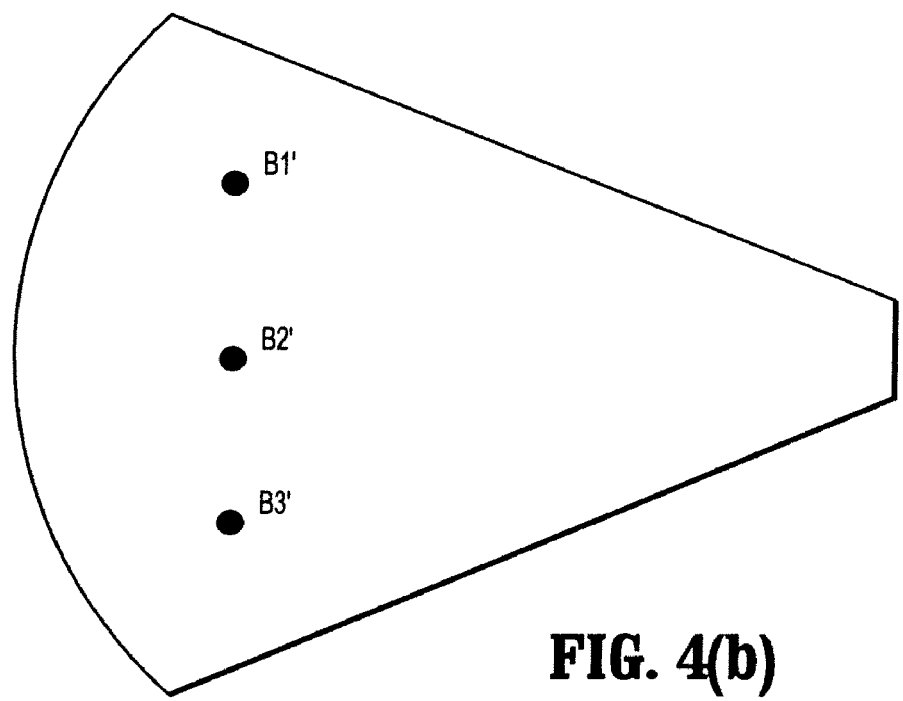

FIG. 4, in parts 4(a) and 4(b), shows schematic ultrasound images corresponding to positions A and respectively B of FIG. 3. The line markers are imaged as dots A1', A2', A3' and respectively B1', B2', B3'. The exact location of positions A and B can be inferred from the ratio of the distances A1'A2' and A2'A3' and respectively B1'B2' and B2'B3', given the geometry of the line marker distribution.

In accordance with a review of the disclosure of the aforementioned provisional application for patent No. 60/718,808, the foregoing principles are extended as follows.

(a) Considering first a multi-catheter calibration chamber, wherein electromagnetic tracking systems are made to track several pose sensors simultaneously. The calibration chamber of FIG. 1 is designed to contain several access guides and several corresponding marker configurations. The access guides are preferably arranged on a circle in the middle of the chamber, and the corresponding marker sets placed around them on the periphery. The magnetic field generator is preferably located underneath the calibration chamber.

As before, the marker geometry needs to be known in the coordinate system of the electromagnetic tracking system. This can preferably be achieved by manufacturing the marker set to a high degree of precision, include several calibration points (for example small notches) on the mechanical set-up, and determine the fixed pose of the marker set in the tracking coordinate system by measuring the coordinates of the notches with pointers that are tracked with the same tracking system.

(b) Considering next a moving marker arrangement in single-catheter calibration chamber: instead of turning the catheter around its axis so that its field of view lines up with the marker configuration, we can rotate the marker configuration around the fixed catheter to achieve suitable constellations. Preferably, the catheter axis is on or near the rotation axis.

For this embodiment, it is necessary to keep track of where the markers are during the rotation. This can be done by placing a pose sensor on the moving platform, or preferably by using a precisely defined rotary motion, where the motor or the shafts are equipped with encoders to report on the current position. One needs to measure the pose of the marker configuration in at least two rotary positions (see (a) above) to determine the rotation axis, and to be able to know the marker positions based on the marker distribution and the encoder reading. The calibration processor has to read in the catheter pose as measured by the pose sensor, the ultrasound image as acquired by the ultrasound transducer, and the rotation information as measured by the encoder.

For efficiency and accuracy, the markers are not only distributed on a single plane, but extend around the catheter. The marker distribution is coded in a bar code fashion so that the calibration processor is able to identify which part of the overall marker distribution is seen in a single image respectively in a sequence of images, retrieve the stored exact geometric configuration, transform it into the coordinate system of the magnetic tracking system according to the encoder reading, and calculate the calibration parameters.

Using a set of string markers as described above around the catheter axis, one can identify the image location from a single image. For greater calibration accuracy, it is preferable to acquire several images and average the results. Continuous or serial operation is possible in which the marker distribution moves continuously around the central axis. Stop-and-go operation is possible (move-acquire data-move-acquire data- . . . ).

"Point markers", as depicted in FIG. 2 cannot be placed densely around the axis. Not all possible 2D images contain relevant information for the calibration process. Stop-and go operation is not practical since one might just image the gaps between the markers. Continuous operation is preferred. Here one records pose, ultrasound, and encoder information at a given rate, and uses the data sequences for calibration. A preferred way of performing the calculations is to observe markers as they enter and leave the ultrasound imaging plane. Using spherical markers, one determines a 2D marker center as it appears in the ultrasound images. As the marker moves through the ultrasound plane, its size grows and shrinks again. One determines the moment in time, or the respective corresponding location of the marker, when it lies directly in the ultrasound plane by finding the maximum marker size. For each passing marker, one establishes a correspondence between a 2D marker location in the image and a 3D marker location in the coordinate system of the magnetic tracker. As described above, a set of these 2D-3D point correspondences allows one to calculate the calibration parameters.

(c) Considering next a multi-catheter calibration chamber with a moving marker arrangement, we can combine the teachings of (a) and (b). It is efficient to be able to acquire calibration information for several catheters in parallel, using the same calibration chamber. The rotating marker arrangement allows one to take more markers and views of the markers into account for the calibration process than would be possible with a single view method.

What we lose in (c) as compared to (a) is the freedom to insert the catheter with an arbitrary orientation around its axis. Once there are more catheters clustered together, one needs to pre-align each catheter around its axis so that it faces the marker distribution and not the other catheters (or the access guides). This pre-alignment can be done automatically, with an appropriate motorized mechanical catheter holder, and with the calibration processor using image processing to identify good and bad viewing directions. The pre-alignment process can be simplified by making the access guides non-transparent in the "bad" or unsuitable viewing direction, and transparent (or open) only in allowed viewing directions.

(d) Considering next a calibration chamber with moving catheters: instead of rotating the markers, one can also rotate the access guides with the catheters, in a way that they keep facing the markers. An advantage is that the markers are fixed in the coordinate system of the magnetic tracking system, and their pose need be determined only once. The movement of the catheters is tracked by their integrated pose sensors. One does not need encoders to keep track of the rotation information. Furthermore, the sensors sample a larger space within the workspace of the magnetic tracking system, and do not rely on a single tracker reading. This makes (d) potentially more precise than (b)/(c). The rotation movement has to be slow, because the reading of the electromagnetic tracking system introduces pose errors with faster sensor movement.

(e) Considering next an outside-in configuration: instead of having the catheters in the middle, surrounded by the marker configuration, one can instead place the marker configuration in the middle, and the access guides with the catheters on the periphery. Again, pre-alignment of the catheters around their axes is necessary to make them face the markers. The system of (e) has the advantage that the markers' configuration is more compact and can be fabricated more easily. Size limitation of the workspace of the electromagnetic tracking system is a design consideration.

(f) Considering next sampling an electromagnetic tracking space by employing multiple field generators. If the catheter is placed in a fixed pose within the workspace of the electromagnetic tracking system, local field non-uniformities can lead to tracking errors, which in turn result in calibration errors. One way to overcome this is to have an arrangement of field generators that can be employed sequentially, and then to average the redundant pose information.

(g) Automation plays a central role in mass calibration. Following is a list of tasks that can potentially be automated with suitable motorized mechanical systems:

insert catheter into and extract from calibration chamber;

pre-align the catheters (turning them around their axes to face the markers);

connect and disconnect the electrical cables between the catheters and the calibration system; and help to keep the catheters sterile, or sterilize them after acquisition of the calibration data;

package the sterile catheters after the calibration process.

Evaluation of the ultrasound images can be completely automated with suitable image processing, including:

finding markers in the image;

finding marker centers; and determining marker size.

In accordance with principles of the invention, a calibration phantom with line-shaped markers is next described.

In accordance with the foregoing, the ultrasound transducer is preferably located in the center of the phantom, aligned with the axis of the calibration phantom, which has a cylindrical hull. The transducer/catheter is either rotated around its axis, or the calibration phantom is rotated around its axis. A plurality of 2D ultrasound images is acquired, showing different views of the calibration phantom.

In contrast to the ball-shaped marker configurations previously disclosed, all the ultrasound images acquired from the line-shaped phantom contribute information for the calibration process. There are no gaps leading to "empty" ultrasound images.

In contrast to the string-based phantom described earlier, the marker lines in the new calibration phantom are not straight, but rather wrap around a center.

The line-shaped calibration phantom contains one or more line objects, wrapped about or around a central axis. As the ultrasound transducer, which is located near the axis, rotates around its axis, the cross-sections of the line objects are seen in the ultrasound images.

A preferred shape for the cross-section is a V, with the tip or point of the V pointing towards the transducer. The tip is thus defined by the intersection point of the straight "arms" of the V-shape and can therefore be accurately placed. FIGS. 5 (*a*) and (*b*) show ultrasound images with such a V-shaped marker cross-sections. Automatic localization of the V and its tip in the 2D image can be performed with methods known in the art, using edge filtering and template matching.

A preferred configuration of the line-shaped markers comprises a set of modulated circles around a common axis. The circles are centered on this axis. To break the rotational symmetry of this configuration, we modulate the shape of the circles, i.e. the true curves are not simply round circles, but rather they comprise curves that swing back and forth around circular lines. In a conveniently simple embodiment, we add a periodic modulation to the radius and/or height of each circle, periodic with regard to the angle around the axis. More complex shapes can be generated.

If the z-axis represents the common axis for the circles in a Cartesian coordinate system, a periodically modulated circle can be described by the following parametric equation:

$$x(\phi)=\cos(\phi)(r+a\cdot\sin(n\cdot\phi+p))$$

$$y(\phi)=\sin(\phi)(r+a\cdot\sin(n\cdot\phi+p))$$

$$z(\phi)=a_z\cdot\sin(n_z\cdot\phi+p_z)+c_z$$

where $\phi\{-\pi,\pi\}$, n and $n_z \in N$, and r is the circle radius. The modulation amplitudes for radius r and height Z are a and $a_z$, and the parameters n and $n_z$ describe how many full periods of modulation occur on the circle, and p and $p_z$ allow for phase shifts of the modulation. FIG. 6 shows an example of three modulated circles in different views in 3D.

To evaluate a set of ultrasound images of the calibration phantom, we first extract for each 2D ultrasound image the 2D coordinates of the tips of the V-shaped marker cross-sections by image processing methods known in the art, such as edge filtering, and template matching, and store this information in conjunction with the position and orientation given by the magnetic tracking sensor.

Then one calculates the calibration parameters, the relative pose of the magnetic tracking sensor and 2D ultrasound image by minimizing the sum of distances of the measured tip points to the circles in 3D. The sum of distances can be minimized with optimization algorithms known in the art, such as Powell-Brent, and Best Neighbor.

Thus $$C = \arg\min \Sigma_i D(T_i C P_i)$$

where

D is a function that returns for each point in 3D the minimal distance to the closest modulated circle in 3D;

$P_i=(x_{2D}, y_{2D}, 0, 1)^T$ is a 4×1 vector with the 2D coordinates of the i-th measured tip point;

$T_i$ is a 4×4 transformation matrix, containing the position and orientation of the magnetic tracking sensor in world coordinates for the i-th measured 2D tip point; and C is a 4×4 transformation matrix, containing the relative pose of the magnetic tracking sensor and 2D ultrasound image.

Instead of, or in addition to the modulation, circles can also be placed off-center from the common axis. It is important to create a marker configuration that is non-periodic around the axis. That is, the combination of circles does not exhibit periodicity within a single complete rotation around the axis. An ultrasound image taken from the axis, with the transducer approximately aligned with the axis, shows a distribution of marker intersections that uniquely depends on the direction around the axis, where the transducer is acquiring the image.

In a preferred way, the calibration phantom is designed with a CAD program, and manufactured with a 3D printing process or computer numerically controlled (CNC) milling.

The present invention has been described by way of embodiments utilizing a B-mode transducer. However, instead of a B-mode transducer, a 2D transducer array that directly captures 3D ultrasound images can also be used. Magnetic tracking still provides the advantages of compounding of 3D image with larger field-of-view, and observing the position of a second magnetically tracked catheter even if it is not in an active ultrasound field-of-view The described method in accordance with the present invention can also be applied to organs other than the heart. For example, one may put a catheter-based ultrasound transducer in the hepatic vein or artery to support liver interventions. One may also use magnetically tracked laparoscopic ultrasound or transrectal ultrasound. The calibration principles of the present invention remain effective and applicable with such changes.

As will be apparent, the present invention is best intended to be implemented with the use and application of imaging equipment in conjunction with a programmed digital computer. The present invention has also been explained in part by way of examples using illustrative exemplary embodiments. It will be understood that the description by way of exemplary embodiments is not intended to be limiting and that, while the present invention is broadly applicable, it is nevertheless helpful to also illustrate its principles, without loss of generality, by way of exemplary embodiments.

It will also be understood that various changes and substitutions not necessarily herein explicitly described may be made by one of skill in the art to which it pertains. Such changes and substitutions may be made without departing from the spirit and scope of the invention which is defined by the claims following.

What is claimed is:

1. Apparatus for calibrating an ultrasound transducer providing B-scans for two-dimensional (2D) images, said apparatus comprising:
   a sensing device attached to said transducer, said sensing device cooperating with a fixed sensing unit for providing an output for labeling respective B-scans with their respective relative positions and orientations (poses);
   a calibration phantom bath including a phantom therein, said transducer being immersed in said bath for imaging said phantom;
   said phantom comprising a line object with distinctive encoding indicative of position along said line object, said line object being generally disposed about an axis substantially concentric with an axis of rotation of said transducer and in the field of view of said transducer;
   means for enabling rotation of one of said transducer and said phantom about said axis of rotation for obtaining successive B-scan images of said line object exhibiting said distinctive encoding;
   means for deriving relative transducer pose information from said distinctive encoding in said successive B-scan images; and
   means for deriving transducer pose information relative to said fixed sensing unit by combining said output thereof and said relative transducer pose information.

2. Apparatus in accordance with claim 1, wherein said means for enabling relative rotation between said transducer and said phantom produces rotation of said transducer about said axis of rotation.

3. Apparatus in accordance with claim 1, wherein said line object forms a loop in a generally circumferential form about said axis.

4. Apparatus in accordance with claim 1, wherein said line object exhibits a cross-section sufficient for providing an adequate ultrasound image in said B-scan images.

5. Apparatus in accordance with claim 1, wherein said line object exhibits a cross-section having a V-shape exhibiting a point.

6. Apparatus in accordance with claim 5, wherein said point is oriented towards said transducer.

7. Apparatus in accordance with claim 5, including means for processing said ultrasound image of said point and said V-shaped cross section for enabling automatic localization of said ultrasound image of said point.

8. Apparatus in accordance with claim 7, including means for performing said automatic localization of said ultrasound image of said point.

9. Apparatus in accordance with claim 1, wherein said encoding comprises said line object being formed into a modulated circular form exhibiting a varying amount of modulation along its length.

10. Apparatus in accordance with claim 1, wherein said line object comprises a plurality of closed loops in a generally circumferential form about said axis.

11. Apparatus in accordance with claim 1, wherein said line object comprises a plurality of loops with a cross-section sufficient for providing an adequate ultrasound image in said B-scan images.

12. Apparatus in accordance with claim 11, wherein said loops have a cross-section having a V-shape exhibiting a point oriented towards said transducer.

13. Apparatus in accordance with claim 12, wherein said loops comprise a corresponding plurality of modulated circular forms exhibiting respective varying amounts of modulation along their respective lengths as a function of angular position around said axis.

14. Apparatus in accordance with claim 13, wherein said loops comprise a corresponding plurality of modulated circular forms exhibit respective varying amounts of modulation along their respective lengths.

15. Apparatus in accordance with claim 14, wherein said modulated circular forms exhibit respective degrees of radial swinging relative to an unmodulated radial line.

16. Apparatus method in accordance with claim 14, wherein said modulated circular forms exhibit respective degrees of swinging up and down relative to an unmodulated circular line.

17. Apparatus in accordance with claim 14, wherein said modulated circular forms exhibit respective degrees of swinging up and down relative to an unmodulated circular line, wherein a given modulated circular form is described as follows:

if the z-axis represents a common axis for circles in a Cartesian coordinate system, a periodically modulated circle can be described by the following parametric equation:

$$x(\phi)=\cos(\phi)(r+a\cdot\sin(n\cdot\phi+p))$$

$$y(\phi)=\sin(\phi)(r+a\cdot\sin(n\cdot\phi+p))$$

$$z(\phi)=a_z\cdot\sin(n_z\cdot\phi+p_z)+c_z$$

where $\phi \in \{-\pi,\pi\}$, n and $n_z \in N$, and r is the circle radius and the modulation amplitudes for radius r and height Z are a and $a_z$, and the parameters n and $n_z$ describe how many full periods of modulation occur on the circle, and p and $p_z$ allow for phase shifts of said modulation.

18. Apparatus in accordance with claim 14, wherein said modulated circular forms exhibit a configuration of said respective varying amounts of modulation that does not exhibit periodicity within a complete rotation around said axis.

19. A method for line-based calibration of an ultrasound transducer for two-dimensional (2D) images, said method comprising:
immersing a transducer in a calibration phantom bath;
encoding a calibration parameter at respective portions of a line object such that said parameter is indicative of a respective associated portion of said line object;
wrapping said line object circumferentially about a substantially concentric axis with said transducer in said bath such that said line object is visible in successive 2D images as said transducer is rotated about said axis;
deriving values of said calibration parameter from respective 2D images; and
calculating the pose of a 2D image from a respective value of said calibration parameter.

20. A method for deriving the pose of a two-dimensional (2D) ultrasound image from a transducer, said method comprising:
setting up a known tracking system having a known coordinate correspondence with a calibration phantom bath;
calculating the pose of said calibration phantom bath;
immersing a transducer in said calibration phantom bath;
encoding a calibration parameter at respective portions of a line object such that said parameter is indicative of a respective associated portion of said line object;
wrapping said line object about a substantially concentric axis with said transducer in said bath such that said line object is visible in successive 2D images as said transducer is rotated about said axis;
deriving values of said calibration parameter from respective 2D images;
calculating a pose of a given 2D image relative to said calibration phantom bath from a respective value of said calibration parameter derived from said given 2D image; and
calculating a pose of said given 2D image relative to said tracking system by utilizing said pose of a given 2D image relative to said calibration phantom bath.

21. A method for calibrating an ultrasound transducer providing B-scans for two-dimensional (2D) images, said method comprising:
attaching to said transducer a sensing device cooperating with a fixed sensing unit for providing an output for labeling respective B-scans with their respective relative positions and orientations (poses);
immersing said transducer in a calibration phantom bath for imaging a phantom;
encoding a line object with distinctive calibration characteristics indicative of position along said line object;
wrapping said line object about an axis substantially concentric with an axis of rotation of said transducer and in the field of view of said transducer;
rotating said transducer about said axis of rotation for obtaining successive B-scan images of said line object exhibiting said calibration characteristics;
deriving relative transducer pose information from said calibration characteristics in said successive B-scan images; and
deriving transducer pose information relative to said fixed sensing unit by combining said output thereof and said relative transducer pose information.

22. A method in accordance with claim 21, wherein said step of wrapping said line object comprises forming said line object into a loop in a generally circumferential form about said axis.

23. A method in accordance with claim 21, wherein said step of wrapping said line object comprises forming said line object with a cross-section sufficient for providing an adequate ultrasound image in said B-scan images.

24. A method in accordance with claim 21, wherein said step of wrapping said line object comprises forming said line object with a cross-section having a V-shape exhibiting a point.

25. A method in accordance with claim 24, wherein said step of forming said line object with a cross-section having a V-shape comprises orienting said point towards said transducer.

26. A method in accordance with claim 25, including a step of automatically localizing said V-shape by processing said V-shape to determine a location of said point.

27. A method in accordance with claim 21, wherein said step of encoding a line object comprises forming said line object into a modulated circular form exhibiting a varying amount of modulation along its length.

28. A method in accordance with claim 21, wherein said step of wrapping said line object comprises forming said line object into a plurality of loops disposed in a generally circumferential form about said axis.

29. A method in accordance with claim 28, wherein said step of wrapping said line object comprises forming said plurality of loops with a cross-section sufficient for providing an adequate ultrasound image in said B-scan images.

30. A method in accordance with claim 28, wherein said step of forming said loops with a cross-section having a V-shape exhibiting a point oriented towards said transducer.

31. A method in accordance with claim 28, wherein said step of forming said plurality of loops comprises forming said loops into a corresponding plurality of modulated generally circular forms exhibiting respective varying amounts of modulation along their respective lengths.

32. A method in accordance with claim 31, wherein said step of forming said loops into a corresponding plurality of modulated circular forms comprises forming said modulated circular forms such that a configuration of said respective varying amounts of modulation does not exhibit periodicity within a complete rotation around said axis.

33. A method in accordance with claim 21, wherein said step of deriving relative transducer pose information from said calibration characteristics in said successive B-scan images comprises extracting for each 2D ultrasound image 2D coordinates of said point exhibited by said V-shape cross-sections by image processing methods.

* * * * *